United States Patent [19]

Colman et al.

[11] Patent Number: 5,428,020
[45] Date of Patent: Jun. 27, 1995

[54] CYSTEINE (NPYS)-CONTAINING PEPTIDES AND USE THEREOF FOR INHIBITING PLATELET AGGREGATION

[75] Inventors: Robert W. Colman, Moylan; Rajinder N. Puri, Philadelphia, both of Pa.; Rei Matsueda, 5-23-2 Matsubara, Setagaya-ku, Tokyo, 156; Hideaka Umeyama, Sanraitopasutoraru 2-C-609, Shinmatsudo 6-70, Matsudo-shi, both of Japan

[73] Assignees: Rei Matsueda; Hideaki Umeyama, both of Japan

[21] Appl. No.: 226,235

[22] Filed: Apr. 11, 1994

Related U.S. Application Data

[63] Continuation of Ser. No. 499,245, Mar. 23, 1990, abandoned.

[51] Int. Cl.$^6$ .................. A61K 38/00; C07K 7/00; C07K 7/06
[52] U.S. Cl. .................................... 514/17; 530/321
[58] Field of Search ..................... 514/17; 530/329

[56] References Cited

U.S. PATENT DOCUMENTS 4,661,471 4/1987 Hawiger et al. ............... 514/13
4,683,291 7/1987 Zimmerman ..................... 530/324

OTHER PUBLICATIONS

Sasaki et al., *Biol Chem.* 259, 12849–54 (1984).
Puri et al., "Selective Inhibition of Thrombin- and Plasmin-Induced Platelet Aggregation and Cleavage of Aggregin by Synthetic Peptide Disulfides", Clinical Research 37 (2), 603A (Apr., 1989).
Puri et al., "Selective Inhibition of Thrombin- and Plasmin-Induced Platelet Aggregation by Phe-Gln-Val-Val-Cys (NpyS)-Gly-NH$_2$—An Examination of the Sequence Specificity", Blood 74(7), Suppl. 1, p. 287a (Nov. 1989).
Matsueda et al., Chem. Lett. 1857–1860 (1988).
Tenno et al., Int. J. Peptide Protein Res. 30, 93–98 (1987).

Matsueda et al., Chem. Lett. No. 2, 191–194 (Feb. 1990).
Matsueda et al., Abstract P1-A25 Kinins '87 Tokyo International Congress (1987).
Kimura et al., Analytical Biochemistry 122, 274–282 (1982).
Matsueda et al., "Cysteine Protease Inhibitors with S-(3-nitro-2-pyridinesulfenyl)-cysteine Residue in Affinity Analogs of Peptide Substrates", Kinins V Part B, Plenum Pub. Corp. (Sep. 1989), pp. 265–270.
Salvesin et al., Biochem. J. 234, 429–434 (1986).
Müller-Esterl, Atemw. Lungenkrkh., Jahrgang 14, 1 Supp.—Heft, S11–S22 (1988).
Kellerman et al., J. Biochem. 154, 471–478 (1986).

*Primary Examiner*—Jill Warden
*Assistant Examiner*—S. G. Marshall
*Attorney, Agent, or Firm*—Seidel Gonda Lavorgna & Monaco

[57] ABSTRACT

Peptides and pharmaceutically acceptable salts thereof of the following formula are provided

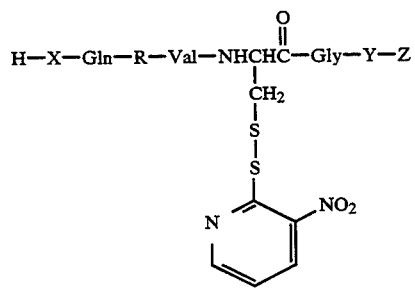

wherein
R is selected from the group consisting of Leu, Ile and Val,
X is from zero to four amino acids,
Y is from zero to four amino acids, and
Z is OH or NH$_2$.

The compounds are useful in inhibiting thrombin- and plasmin-induced aggregation of human platelets.

36 Claims, No Drawings

CYSTEINE (NPYS)-CONTAINING PEPTIDES AND USE THEREOF FOR INHIBITING PLATELET AGGREGATION

Reference to Government Grant

The invention described herein was made, in part, in the course of work under National Institutes of Health Grant HL-36579.

This is a continuation of application Ser. No. 07/499,245, filed Mar. 23, 1990, now abandoned.

FIELD OF THE INVENTION

The invention relates to inhibition of human platelet aggregation. In particular, the invention relates to inhibition of platelet aggregation with synthetic peptides.

BACKGROUND OF THE INVENTION

Activation and aggregation of human platelets leads to the formation of blood clots (thrombi). It is well established that the binding of fibrinogen to specific receptors on platelets is essential for platelet aggregation. Unstimulated platelets do not bind fibrinogen and do not aggregate during circulation. When platelets are stimulated by certain physiological agonists, such as ADP, thrombin, etc., the fibrinogen receptors associated with the glycoprotein IIb/IIIa complex on the platelet become exposed, resulting in fibrinogen binding leading to platelet aggregation.

Aggregen ($M_r = 100$ kDa) is a putative ADP-receptor on the platelet surface. It has been shown to be completely cleaved during thrombin- and plasmin-induced platelet aggregation. The binding of thrombin and plasmin to their receptors on the platelet surface is a important requirement for these plasma proteases to elicit aggregen proteolysis and platelet aggregation.

Thrombin- and plasmin-induced platelet aggregation and cleavage of aggregen are indirectly mediated by intracellularly activated calpain expressed on the platelet surface. Thrombin- and plasmin-induced platelet aggregation are inhibited by cysteine protease inhibitors, including high molecular weight kininogen. The latter is also an inhibitor of platelet calpain.

Matsueda et al., Chem. Lett. 1857–1860 (1988) disclose synthetic peptides containing a S-(3-nitro-2-pyridinesulfonyl)-cysteine residue which have activity as inhibitors of cathepsin B. The latter is an intracellular proteolytic enzyme which belongs to the group of closely related thiol proteases including cathepsin H and L.

The heavy chain of high molecular weight kininogen contains three repeating units having mutual sequence homology, designated D1, D2, and D3. Of these three repeats, D2 and D3 contain the pentapeptide Gln-Val-Val-Ala-Gly ("QVVAG"). D2 and D3 are inhibitors of cysteine proteases, with D2 being effective in inhibiting calpain, Salvesen et al., Biochem. J. 234, 429–434 (1986); Muller-Esterl Atemw.-Lungenkrkh. Jahrgang 14, 1.Suppl.-Heft S11–S22 (1988). Although the inhibitory activity of high molecular weight kininogen and other cysteine protease inhibitors have been attributed to the QVVAG sequence, it has never been demonstrated that the pentapeptide alone has inhibitory activity against calpain. Teno et al., Int. J. Peptide Protein Res. 30, 93–98 (1987) report weak activity of the QVAAG pentapeptide in inhibiting the thiol protease papain.

Reocclusion of coronary arteries is a frequent complication following thrombolytic therapy. It has been postulated that reocclusion is due to plasmin-induced activation of platelets. High concentrations of plasmin, such as might occur in therapeutic thrombolysis, are known to cause platelet aggregation.

Coronary artery restenosis following angioplasty has been linked to platelet activation by protease agonists. Restenosis may be initiated by thrombin-stimulated release of growth factors from platelets.

What is needed is a method of inhibiting stimulation and aggregation of platelets by protease agonists, specifically a method of inhibiting stimulation of platelets by inhibiting the action of platelet calpain in facilitating thrombin- and plasmin-induced platelet aggregation.

SUMMARY OF THE INVENTION

Peptides and pharmaceutically acceptable salts thereof of the following formula are provided:

$$H-X-Gln-R-Val-NHCH(CH_2-S-S-\text{(3-nitro-2-pyridyl)})C(O)-Gly-Y-Z$$

wherein

R is selected from the group consisting of Leu, Ile and Val, preferably Val,

X is from zero to four amino acids,

Y is from zero to four amino acids, and

Z is OH or $NH_2$.

According to a subgeneric aspect of the invention, peptides of the above formula are provided wherein X is a single amino acid selected from the group consisting of Arg, Phe, Trp, Tyr, Nal, Asp, and Ala, preferably Arg, Phe and Ala; and R and Z are as defined above.

According to another subgeneric aspect of the invention, peptides of the above formula are provided wherein Y is zero amino acids, Z is $NH_2$, and R and X are defined as above.

The peptides are potent inhibitors of platelet aggregation.

A method of inhibiting thrombin- or plasmin-induced aggregation of human platelets is provided, comprising incubating human platelets with one or more of the novel peptides.

By "amino acid" as used herein is meant not only those organic acids containing both a basic amino group ($NH_2$) and an acid carboxyl group (COOH), which have been established as protein constituents, but also includes such acids which have been modified by attachment of various side groups, such as in the case of 1-naphthylalanine ("Nal").

DETAILED DESCRIPTION OF THE INVENTION

The synthetic peptide disulfides of the invention inhibit the activity of platelet calpain, and thus effectively inhibit thrombin- and plasmin-induced, calpain-mediated human platelet aggregation. The peptides contain the S-(3-nitro-2-pyridinesulfenyl)-cysteine residue ("S-NpyS-Cys"):

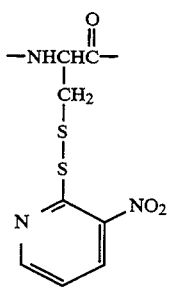

The S-NpyS group of the above cysteine derivative is capable of reacting selectively with the free thiol group of another cysteine-containing peptide, HS-$R_2$, to afford an unsymmetrical disulfide bond as follows:

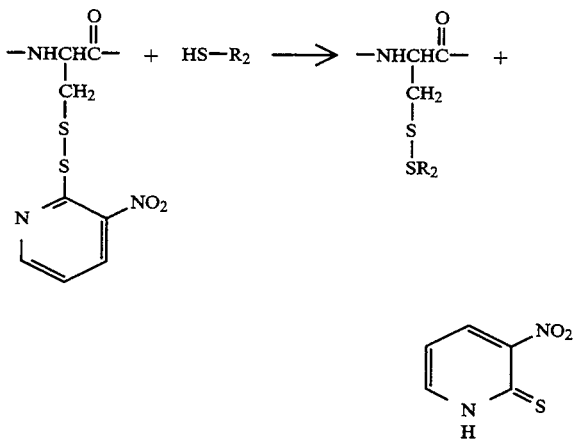

Without wishing to be bound by any theory, it is believed that the peptides of the present invention selectively bind to regions in the vicinity of thiol groups in platelet calpain, effectively inhibiting the protease activity of calpain, which activity is believed responsible for the mediation of thrombin- and plasmin-induced platelet aggregation.

The peptides described herein were prepared by the solid phase method utilizing tert-butyloxycarbonyl protected amino acids ("Boc amino acids") according to the general procedure of Stewart and Young, Solid Phase Peptide Synthesis, Pierce Chemical Company, Rockford, Ill. (1984). Thus, the peptides of the present invention are prepared by combining the C-terminus of individual amino acids or groups of amino acids on a solid phase resin, e.g. benzhydrylamine resin, to yield the desired peptidyl resin intermediate. The amino acid-resin thus containing a free amino group is subject to chain extension by reaction with the activated carboxylic group of another Boc-protected amino acid. The carboxylic group of such Boc-protected amino acids may be activated by, for example, 1-hydroxybenzotriazole ester or other suitable activating reagent. The Boc-protected and activated amino acid intermediate is permitted to react with the free amino group of the amino acid-resin, thus extending the peptide chain. After the appropriate number of chain extensions are carried out, the peptide is then removed from the resin support by treatment with a reagent, typically an acid. Hydrogen fluoride is particularly suitable since it not only cleaves the peptide from the resin, but also cleaves remaining side-chain protecting groups. The peptides may then be purified by various known chromatographic techniques.

Boc-amino acids for use in the practice of the invention are commercially available, e.g. from the Peptide Institute Inc., Osaka, Japan, and from Bachem Freinchemikalein AG, Switzerland. Boc-amino acids may be synthesized by any of the various known methods, such as the methods summarized by Stewart and Young, Solid Phase Peptide Synthesis, p.61–63. Boc-protected Cys(NpyS), that is, N-t-butyloxycarbonyl-S-(3-nitro-2-pyridenesulfonyl)-cysteine ("Boc-Cys(NpyS)-OH") may be prepared from Boc-Cys(SH)-OH by reaction with 3-nitro-2-pyridenesulfonyl halides, or by conversion of conventional S-protecting groups such as benzyl-t-butyl, acetamidomethyl or trityl into S-(3-nitro-2-pyridenesulfonyl) groups by reaction with 3-nitro-2-pyridenesulfonyl halides according to Matsueda et al., Chem. Lett. 737 (1981) and Matsueda et al., Chem. Lett. 921 (1982).

The preparation of the synthetic peptides of the present invention is illustrated by the following non-limiting examples. The free base of the exemplified trifluoroacetic acid ("TFA") salts may be prepared by treating the acid salt with an appropriate base.

EXAMPLE 1

TFA.H-Phe-Gln-Val-Val-Cys(NpyS)-Gly-$NH_2$

The Boc derivatives of Gly, Cys(NpyS), Val, Gln and Phe were coupled successively in dimethylformamide with three equivalents of dicyclohexylcarbodiimide and six equivalents of 1-hydroxybenzotriazole to benzhydrylamine resin (0.2g, 1.04 mmol) (Peptide Institute Inc., Osaka, Japan). Three equivalents of each amino acid were utilized. The Boc groups were removed with trifluoroacetic acid in $CH_2Cl_2$ (1:1 v/v). A coupling period of 2–5 hours was utilized. The completion of the couplings was judged by the method of Kaiser et al., Anal. Biochem. 34, 595 (1970). The finished peptide resin was dried and treated with 20 ml of HF containing 2 ml of anisole for thirty minutes at 0° C. After removal of the HF, the resin was washed with several portions of ether and the liberated peptide was extracted twice with 30 ml of TFA. The solvent was removed and the residue was treated with ether. The crude product was purified with Sephadex ® LH-20 in methanol, or by high performance liquid chromatography on a C-18 column utilizing a linear gradient of 0.1% TFA in water to 50% acetonitrile in water containing 0.1% TFA over sixty minutes at a flow rate of 7 ml/min. Yellow fractions containing a single spot upon thin layer chromatography where pooled and evaporated. The title compound was obtained as the trifluoroacetic acid salt $C_{36}H_{49}O_{11}N_{10}S_2F_3.2H_2O$ by precipitation from methanol-ether-petroleum ether, 415 mg, 42% yield from the initial resin. M.p. 230°–234° C. (dec.); $[\alpha]^{22}_D = -75.6°$ (c 0.2, MeOH). The amino acid ratios were as follows: $CysO_3H$, 1.01; Glu, 1; Gly, 1.14; Val, 1.88; Phe, 0.92; $NH_3$, 1.28. Elemental analysis, calcd: C, 45.28: H, 5.59; N, 14.67; S, 6.72; F, 5.97. Found: C, 45.09; H, 5.35; N, 14.47, S, 6.91; F, 6.01. $Rf_1/Rf_2 = 0.12/0.69$ for BuOH:AcOH:$H_2O$(4:1:1)-/BuOH:AcOH:pyridine (30:6:24:20) on Kieselgel G. Merck plates.

EXAMPLE 2

TFA.H-Phe-Gln-Leu-Val-Cys(NpyS)-Gly-NH$_2$

The procedure of Example 1 was followed utilizing Boc derivatives of Gly, Cys(NpyS), Val, Leu, Gln and Phe to provide the title compound as $C_{37}H_{51}O_{11}N_{10}S_2F_3.2H_2O$. M.p. 227°~229° C. (dec.); $[\alpha]^{22}_D = 78.1°$ (c 0.2, MeOH); Rf$_1$/Rf$_2$=0.28/0.65; Amino acid ratios: Phe, 0.99; Glu, 1.01; Leu, 0.96; Val, 0.94; CysO$_3$H, 0.91; Gly, 1; NH$_3$, 1.41. Calcd: C, 45.86; H, 5.72; N, 14.46; S, 6.62, F, 5.88. Found: C, 46.01; H, 5.81; N, 14.32; S, 6.50; F, 5.93.

EXAMPLE 3

TFA.H-Arg-Gln-Val-Val-Cys(NPYS)-GlY-NH$_2$

The procedure of Example 1 was followed utilizing Boc derivatives of Gly, Cys(NpyS), Val, Val, Gln and Arg to provide the title compound as $C_{35}H_{53}O_{13}N_{13}S_2F_6.2H_2O$. M.p. 218°~221° C. (dec.); $[\alpha]^{22}_D = -86.5°$ (c 0.2, MeOH); Rf$_1$/Rf$_2$=0.03/0.50. Amino acid ratios: Glu, 1; Gly, 1.00; Val, 1.87; Arg, 0.91; CysO$_3$H, 0.81; NH$_3$, 1.39. Calcd: C, 38.99; H, 5.29; N, 16.89; S, 5.95; F, 10.58. Found: C, 39.05; H, 5.12; N, 16.85; S, 6.03; F, 10.38.

EXAMPLE 4

TFA.H-Ala-Gln-Val-Val-CYs (NpyS)-GlY-NH$_2$

The procedure of Example 1 was followed utilizing Boc derivatives of Giy, Cys(NpyS), Val, Val, Gln and Ala to provide the title compound as $C_{30}H_{45}O_{11}N_{10}S_2F_3.2H_2O$. M.p. 235°~238° C. (dec.); $[\alpha]^{22}_D = -106.7°$ (c 0.2, MeOH); Rf$_1$/Rf$_2$=0.11/0.58. Amino acid ratios: Glu, 1; Gly, 0.97; Val, 1.88; Ala, 0.97; CysO$_3$H, 0.81; NH$_3$, 1.42. Calcd: C, 40.99; H, 5.62; N, 15.94; S, 7.30; F, 6.49. Found: C, 40.74; H, 5.31; N, 15.82; S, 7.48; F, 6.54.

EXAMPLE 5

TFA.H-Gln-Val-Val-Cys(NpyS)-Gly-NH$_2$

The procedure of Example 1 was followed utilizing Boc derivatives of Gly, Cys (NpyS), Val, Val and Gln to provide the title compound as $C_{27}H_{40}O_{10}N_9S_2F_3.2H_2O$. M.p. 229°~231° C. (dec.); $[\alpha]^{22}_D = -132.6°$ (c 0.2, MeOH); Rf$_1$/Rf$_2$=0.14/0.72. Amino acid ratios: Glu, 1; Val, 1.99; CysO$_3$H,H, 0.81; Gly, 1.02; NH$_3$, 1.29. Calcd: C, 40.14; H, 5.49; N, 15.61; S, 7.94; F, 7.06. Found: C, 40.34; H, 5.58; N, 15.60; S, 7.81; F, 7.29.

EXAMPLE 6

TFA.H-Nal-Gln-Val-Val-Cys(NpyS)-Gly-NH$_2$

The procedure of Example 1 was followed utilizing Boc derivatives of Gly, Cys(NpyS), Val, Val, Gln and Nal to provide the title compound as $C_{40}H_{51}O_{11}N_{10}S_2F_3.2H_2$. M.p. 237°~240° C. (dec.); $[\alpha]^{22}_D = -136.2°$ (c 0.2 MeOH); Rf$_1$/Rf$_2$=0.13/0.83. Amino acid ratios: Nal, 0.92; Glu, 1.03; Val, 1.92; CysO$_3$, 1.04; Gly, 1; NH$_3$, 1.52. Calcd: C, 47.81; H, 5.51; N, 13.94; S, 6.38; F, 5.67. Found: C, 47.68; H, 5.71; N, 13.77; S, 6.31; F, 5.79.

EXAMPLE 7

TFA.H-Asp-Phe-Gln-Val-Val-Cys(NpyS)-Gly-NH$_2$

The procedure of Example 1 was followed utilizing Boc derivatives of Gly, Cys(NpyS), Val, Val, Gln, Phe and Asp to provide the title compound as $C_{48}H_{54}O_{14}N_{11}S_2F_3.2H_2O$. M.p.217°~220° C. (dec.); $[\alpha]^{22}_D = -29.1°$ (c 1.2, DMF); Rf$_1$/Rf$_2$=0.21/0.54. Amino acid ratios: Asp, 0.96; Phe, 0.97; Glu, 1.01; Gly, 1; Val, 1.95; CysO$_3$H, 0.92; NH$_3$, 1.45. Calcd: C, 44,90; H, 5.46; N, 14.40; S, 5.99; F, 5.33. Found: C, 44.99; H, 5.62; N, 14.28; S, 5.87; F, 5.47.

The calpain-inhibiting activity of the peptides of the invention was demonstrated according to a modification of the procedure of Schmaier et al., J. Clin. Invest. 77, 1565 (1986). A calpain preparation (5~10 μl) was placed on a floating filter membrane (Marusyk et al., Anal. Biochem. 105, 403 (1980)) (Millipore type VMWP) over a buffer containing 50 mM Tris/HCl, pH 7.5 and 2.5 mM EDTA for 45–60 minutes, carefully removed and used for the following inhibition study. Aliquots (25 μl) of the enzyme (calpain) and buffer or synthetic peptide were added to a cuvette at 25° C. containing 1 mM succinyl-Leu-Tyr-amino-4-methylcumarin as the substrate in a buffer consisting of 60 mM Tris/HCl, pH 7.5, 2.5% DMSO and 5 mM CaCl$_2$. The rate of substrate hydrolysis was continuously recorded on a Perkin-Elmer LS-5 fluorescence spectrophotometer connected to a R100 chart recorder. The absorbance maximum of substrate occurred at 380 nm and emission maximum was observed at 450 nm. The IC$_{50}$ was calculated from the dose-dependent curve for each inhibitor. The IC$_{50}$ corresponds to that concentration of inhibitory peptide that produced 50% inhibition of calpain activity. In all cases, 90 mM calpain was utilized. The data is set forth in the following table:

TABLE 1

| Compound | Calpain Inhibitory Potency IC$_{50}$ (M × 10$^{-6}$) |
| --- | --- |
| Example 1 | 4.1 |
| Example 2 | 5.6 |
| Example 3 | 55 |
| Example 4 | 16 |
| Example 5 | 36 |

The platelet aggregation-inhibiting activity of the peptides of the invention was demonstrated in the presence of the following platelet agonists: (1) phorbol myristate acetate ("PMA") , (2) thrombin, (3) plasmin, (4) adenosine diphosphate ("ADP") , (5) collagen, (6) the 9,11-methanol derivative of prostaglandin H$_2$ ("U46619"), and (7) the calcium ionophore A23187 (Calimycin, Calbiochem, San Diego, Calif. ("A23187")). Platelet-rich plasma was prepared by differential centrifugation (120×g, 30 min, 23° C.) of fresh whole human blood drawn into acid/citrate/dextrose (citric acid 0.079 M, sodium citrate, 0.085 M and dextrose 0.180 M) in a ratio of 1 ml of anticoagulant solution per 9 ml of blood. The platelets were washed and their suspensions prepared by a modification of the method of Mustard, et al., Brit. J. Haemat. 22, 193–204 (1972). The modifications included incubation of platelet-rich plasma with prostaglandin E$_1$, hirudin and apyrase and two successive washes of the platelets with Tyrode-albumin buffer (without Ca$^{++}$) containing hirudin and apyrase, and apyrase alone. Platelet aggregation in the presence of each agonist and inhibitor peptide (0.8 nm) was performed at 37° C. under constant stirring (1100 rpm) conditions in a chronolog (Lumi) aggregometer. The total volume of the incubation mixture in the sample cuvette was 500 μl and the platelet concentration was adjusted to 5×10$^8$/ml. The reference cuvette contained the suspension buffer.

Platelet aggregation was initiated by the addition of the agonist to the sample cuvette. The data is indicated in the following table wherein "+" indicates inhibition of platelet aggregation, "−" indicates the absence of inhibition of platelet aggregation, and "partial" indicates a partial inhibition of platelet aggregation.

TABLE 2

| Compound | PMA (0.016 uM) | Thrombin (0.02 uM) | Plasmin (0.025 uM) | ADP (20 uM) | Collagen (4 ug/ml) | U46619 (1 uM) | A23187 (2.5 uM) |
|---|---|---|---|---|---|---|---|
| Example 1 | − | + | + | − | − | − | − |
| Example 2 | partial | + | + | partial | partial | partial | partial |
| Example 3 | + | + | + | + | + | + | partial |
| Example 4 | + | + | + | + | + | + | partial |
| Example 5 | + | + | + | + | + | + | partial |

While each of the peptides of the invention tested inhibit thrombin- or plasmin-induced platelet aggregation, TFA.H-phe-Gln-Val-Val-Cys(NpyS)-Gly-NH₂ (Example 1) did not inhibit aggregation induced by any of the other agonists tested. Thus, this peptide may be utilized to specifically inhibit thrombin- and plasmin-induced platelet aggregation, while otherwise maintaining normal hemostasis. Moreover, the compound had no effect on the platelet shape change introduced by thrombin and plasmin, indicating that it did not effect the ability of the plasma proteases to bind platelets. Moreover, TFA.H-Phe-Gln-Val-Val-Cys(NpyS)-GlY-NH₂ did not inhibit amidolytic activity of thrombin and plasmin, or the fibrinogenolytic activity of thrombin. It did not raise platelet-cAMP levels, but completely inhibited thrombin- and plasmin induced cleavage of [³H]-5′-p-fluorosulfonylbenzoyl adenosine-labeled aggregen in intact radiolabeled platelets.

These results show that the Example 1 peptide, in particular, is a specific inhibitor of thrombin- and plasmin-induced platelet aggregation and cleavage of aggregen. Without wishing to be bound by any theory, it is believed that the mechanism of the Example 1 compound is to inhibit platelet calpain expressed on the platelet surface.

The synthetic peptides of the invention may be administered to subjects in any situation where inhibition of platelet aggregation, in particular inhibition of thrombin- or plasmin-induced platelet aggregation, is desired. Thus, the compounds may be administered during or after angioplasty or thrombolytic therapy to prevent restenosis or reocclusion. It is believed that restenosis following angioplasty may be initiated by thrombin-stimulated release of growth factors from platelets. Reocclusion, a frequent occurrence after thrombolytic therapy, has been postulated to be caused by plasmin-induced activation of platelets.

The synthetic peptides of the present invention may be formulated into pharmaceutical preparations for therapeutic use. To prepare them for intravenous administration, the compounds may be dissolved in an appropriate intravenous delivery vehicle containing physiologically compatible substances such as sodium chloride, glycine and the like having a buffered pH compatible with physiologic conditions. Such intravenous delivery vehicles are known to those skilled in the art.

The peptides may be administered by any convenient means which will result in the delivery to the bloodstream of a platelet calpain-inhibiting effective amount. Intravenous administration is presently contemplated as the preferred administration route. The amount administered will depend on the activity of the particular compound, administered, which may readily be determined by those of ordinary skill in the art. Generally, the peptides may be in an amount sufficient to provide a plasma concentration in the range of from about 10 to about 500 μM, more preferably in the range of from about 50 to 250 μM. Plasma concentrations higher or lower than these may be utilized, depending upon the activity of the particular compound being administered and the nature of the treatment.

The compounds may be administered in the free base form, or, more particularly, may be administered in the form of pharmacologically acceptable salts. Salts may be prepared by treatment with various inorganic or organic acids, such as hydrochloric, hydrobromic, sulfuric, phosphoric, acetic, lactic, succinic, fumaric, malic, maleic, tartaric, citric, benzoic, methanesulfonic or carbonic acids.

The present invention may be embodied in other specific forms without departing from the spirit or essential attributes thereof and, accordingly, reference should be made to the appended claims, rather than to the foregoing specification, as indicating the scope of the invention.

We claim:

1. A peptide of the formula

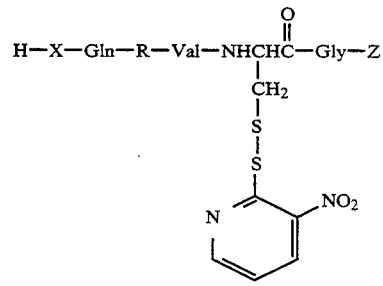

wherein
R is selected from the group consisting of Leu, Ile, and Val,
X is zero amino acids, or X is selected from the group consisting of Arg, Phe, Trp, Tyr, Nal and Ala,
Z is OH or NH₂,
or pharmaceutically acceptable salts thereof.

2. A peptide according to claim 1 wherein R is Val.

3. A peptide according to claim 1 wherein X is a single amino acid selected from the group consisting of Arg, Phe, Trp, Tyr, Nal, and Ala.

4. A peptide according to claim 2 wherein X is a single amino acid selected from the group consisting of Arg, Phe, Trp, Tyr, Nal, and Ala.

5. A peptide according to claim 3 wherein X is a single amino acid selected from the group consisting of Arg, Phe and Ala.

6. A peptide according to claim 4 wherein X is a single amino acid selected from the group consisting of Arg, Phe and Ala.

7. A peptide according to claim 1 wherein Z is $NH_2$.
8. A peptide according to claim 2 wherein Z is $NH_2$.
9. A peptide according to claim 3 wherein Z is $NH_2$.
10. A peptide according to claim 4 wherein Z is $NH_2$.
11. A peptide according to claim 5 wherein Z is $NH_2$.
12. A peptide according to claim 6 wherein Z is $NH_2$.
13. A peptide according to claim 1 wherein the peptide is H-Phe-Gln-Val-Val-Cys(NpyS)-Gly-$NH_2$, or pharmaceutically acceptable salt thereof.
14. A peptide according to claim 1 wherein the peptide is H-Phe-Gln-Leu-Val-Cys(NpyS)-Gly-$NH_2$, or pharmaceutically acceptable salt thereof.
15. A peptide according to claim 1 wherein the peptide is H-Arg-Gln-Val-Val-Cys(NpyS)-Gly-$NH_2$, or pharmaceutically acceptable salt thereof.
16. A peptide according to claim 1 wherein the peptide is H-Ala-Gln-Val-Val-Cys(NpyS)-Gly-$NH_2$, or pharmaceutically acceptable salt thereof.
17. A peptide according to claim 1 wherein the peptide is H-Gln-Val-Val-Cys(NpyS)-Gly-$NH_2$, or pharmaceutically effective salt thereof.
18. A peptide according to claim 1 wherein the peptide is H-Nal-Gln-Val-Val-Cys(NpyS)-Gly-$NH_2$, or pharmaceutically effective salt thereof.
19. A method of inhibiting thrombin- or plasmin-induced aggregation of human platelets comprising incubating human platelets with a peptide of the formula

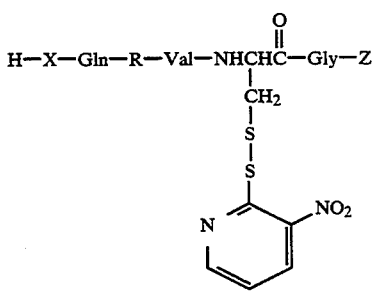

wherein
R is selected from the group consisting of Leu, Ile, and Val,
X is zero amino acids, or X is selected from the group consisting of Arg, Phe, Trp, Tyr, Nal and Ala;
Z is OH or $NH_2$,
or pharmaceutically acceptable salts thereof.
20. A method according to claim 19 wherein R is Val.
21. A method according to claim 19 wherein X is a single amino acid selected from the group consisting of Arg, Phe, Trp, Tyr, Nal, and Ala.
22. A method according to claim 20 wherein X is a single amino acid selected from the group consisting of Arg, Phe, Trp, Tyr, Nal, and Ala.
23. A method according to claim 21 wherein X is a single amino acid selected from the group consisting of Arg, Phe and Ala.
24. A method according to claim 22 wherein X is a single amino acid selected from the group consisting of Arg, Phe and Ala.
25. A method according to claim 19 wherein Z is $NH_2$.
26. A method according to claim 20 wherein Z is $NH_2$.
27. A method according to claim 21 wherein Z is $NH_2$.
28. A method according to claim 22 wherein Z is $NH_2$.
29. A method according to claim 23 wherein Z is $NH_2$.
30. A method according to claim 24 wherein Z is $NH_2$.
31. A method according to claim 19 wherein the peptide is H-Phe-Gln-Val-Val-Cys(NpyS)-Gly-$NH_2$, or pharmaceutically acceptable salt thereof.
32. A method according to claim 19 wherein the peptide is H-Phe-Gln-Leu-Val-Cys(NpyS)-Gly-$NH_2$, or pharmaceutically acceptable salt thereof.
33. A method according to claim 19 wherein the peptide is H-Arg-Gln-Val-Val-Cys(NpyS)-Gly-$NH_2$, or pharmaceutically acceptable salt thereof.
34. A method according to claim 19 wherein the peptide is H-Ala-Gln-Val-Val-Cys(NpyS)-Gly-$NH_2$, or pharmaceutically acceptable salt thereof.
35. A method according to claim 19 wherein the peptide is H-Gln-Val-Val-Cys(NpyS)-Gly-$NH_2$, or pharmaceutically acceptable salt thereof.
36. A method according to claim 19 wherein the peptide is H-Nal-Gln-Val-Val-Cys(NpyS)-GlyL-$NH_2$, or pharmaceutically acceptable salt thereof.

* * * * *